United States Patent [19]

Manami et al.

[11] Patent Number: 4,914,231

[45] Date of Patent: Apr. 3, 1990

[54] METHOD FOR PURIFYING A CRUDE DIPHENYLSULFONE TETRACARBOXYLIC ACID

[75] Inventors: Hiroshi Manami, Jyoyo; Shigeo Miki, Hirakata; Mikio Nakazawa, Uji, all of Japan

[73] Assignee: New Japan Chemical Co., Ltd., Kyoto, Japan

[21] Appl. No.: 245,425

[22] Filed: Sep. 16, 1988

[30] Foreign Application Priority Data

Sep. 19, 1987 [JP] Japan ................................. 62-235749

[51] Int. Cl.$^4$ ............................................. C07C 51/43
[52] U.S. Cl. ...................................... 562/429; 562/430
[58] Field of Search ............................ 560/11, 12, 13; 562/429, 430; 260/701, 707

[56] References Cited

U.S. PATENT DOCUMENTS

| | | | |
|---|---|---|---|
| 3,504,022 | 3/1970 | Bresson | 562/416 |
| 4,287,366 | 9/1981 | Yamaguchi et al. | 562/429 |
| 4,445,124 | 4/1984 | Fujii | 346/75 |
| 4,827,029 | 5/1989 | Kleeman | 562/559 |
| 4,855,218 | 8/1989 | Fujita | 430/428 |

OTHER PUBLICATIONS

Chelates in Analytical Chemistry, vol. 1, Ed. by H. A. Flaschka and A. J. Barnard, Jr., Marcell Dekker, Inc., New York, 1967, pp. 49-79 and 291-292.

Primary Examiner—Michael L. Shippen
Attorney, Agent, or Firm—Armstrong, Nikaido, Marmelstein, Kubovcik & Murray

[57] ABSTRACT

Disclosed is a method for purifying a crude diphenylsulfone tetracarboxylic acid which comprises the steps of dissolving a crude diphenyolsulfone tetracarboxylic acid in a solvent mixture of water and acetic acid and recrystallizing the crude to obtain a highly purifed diphenylsulfone tetracarboxylic acid.

9 Claims, No Drawings

METHOD FOR PURIFYING A CRUDE DIPHENYLSULFONE TETRACARBOXYLIC ACID

BACKGROUND OF THE INVENTION

This invention relates to a method for purifying a crude diphenylsulfone tetracarboxylic acid.

Certain processes have been proposed for preparing diphenylsulfone tetracarboxylic acids (hereinafter referred to as "DSTA"). For example, USSR Patent No.422,730 discloses a process for producing DSTA by oxidizing 3,3',4,4'-tetramethyldiphenylsulfone with molecular oxygen in the presence of a heavy metal catalyst such as a cobalt salt. In practicing such process for an industrial purpose, it becomes necessary to separate the heavy metal catalyst used and undesired byproducts from the resultant crude DSTA in order to recover the expensive heavy metal and to obtain purified DSTA free from the contamination by the heavy metal and byproducts. While these processes give DSTA unavoidably contaminated with impurities such as catalytic components, byproducts and the like, no method has been proposed, nevertheless, for effectively purifying crude DSTA to obtain highly purified DSTA.

SUMMARY OF THE INVENTION

An object of the invention is to provide a new method for purifying crude DSTA by which highly purified DSTA free from undesired impurities is easily obtainable.

The above and other objects of the invention will become apparent from the following description.

The present inventors' investigation has revealed that when crude DSTA is recrystallized from a solvent mixture of water and acetic acid there is provided highly purified DSTA free from impurities such as heavy metals and byproducts.

The present invention provides a method for purifying a crude DSTA which comprises the steps of dissolving the crude in a solvent mixture of water and acetic acid and recrystallizing the crude to obtain a purified DSTA.

DETAILED DESCRIPTION OF THE INVENTION

Throughout the specification and claims, the term "diphenylsulfone tetracarboxylic acids (DSTA)" represents tetracarboxylic acids having the following formula:

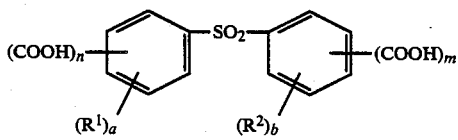

wherein $R^1$ and $R^2$ are each hydrogen, alkyl having 1 to 5 carbon atoms, halogen, nitro, amino, hydroxyl, sulfonic acid residue, alkoxyl having 1 to 5 carbon atoms, phenoxy or substituted phenoxy, m and n are each an integer of 0 to 4, the sum of m and n is 4, a is an integer of 5-n and b is an integer of 5-m.

Examples of DSTA are diphenylsulfone-2,2',3,3'-tetracarboxylic acid, diphenylsulfone-2,3,3',4'-tetracarboxylic acid, diphenylsulfone-3,3',4,4'-tetracarboxylic acid, 2-chlorodiphenylsulfone-3,3',4,4'-tetracarboxylic acid, 2,2'-dichlorodiphenylsulfone-3,3',4,4'-tetracarboxylic acid, 2-methyldiphenylsulfone-3,3',4,4'-tetracarboxylic acid, 2,2'-dimethyldiphenylsulfone3,3',4,4'-tetracarboxylic acid, etc.

The crude DSTA or DSTA crude to be purified in this invention includes unpurified DSTA and reaction products obtained by various processes for synthesizing DSTA. In accordance with the present method the crude DSTA produced by any synthesis process can be purified effectively. For example, the present method can purify any crude DSTA produced by oxidizing the corresponding tetraalkyldiphenylsulfone with an oxidizing agent such as nitric acid, chromic acid, dichromate, permanganate or the like or with air in liquid phase. The crude DSTA usually contains impurities, which are various in accordance with the synthesis process, such as a heavy metal ion used as a catalyst or oxidizing agent, organic solvent, byproducts and the like. The heavy metal ions include, for example, those of Cr, Mn, V, W, Cu, Co, Fe, Ni, Zr, Mo, Ru, Rh, Pd, Pt, Ce, etc.

According to the present invention, the crude DSTA is purified by recrystallization from a solvent mixture of water and acetic acid. The concentration of acetic acid in the solvent mixture is in the range of 2 to 90 vol. %, preferably about 10 to about 70 vol. %.

According to the present invention the DSTA crude to be purified is dissolved in the solvent mixture of water and acetic acid at an elevated temperature ranging from about 40° to about 200° C., preferably about 50° to about 150° C. When crude DSTA contains as an impurity the acetic acid used in the preparation process, the crude can be dissolved only in water to form a solution of the crude in a solvent mixture of water and acetic acid. The amount of the solvent mixture relative to the crude is about 1 to about 200 times, preferably about 3 to about 50 times, the weight of the crude. When used in less than the equal amount, the solvent mixture displays a poor dissolving power when mixed with the crude, while it shows no significant superiority in purifying effect, when used in more than 200 times.

When the crude contains a heavy metal ion, it is preferable to treat the crude with a cation exchange resin or chelating resin prior to the recrystallization step to remove the heavy metal ion more effectively from the crude. In this case the solution of DSTA crude in the mixed solvent is passed a column packed with the resin, or the resin is added to the crude solution and mixed thoroughly, followed by filtration or centrifugation. Preferred examples of the cation exchange resins are "DIAION-SK", "DIAION-PK" (each a trade name, product of Mitsubishi Kasei Corporation, Japan), Duolite-C (trade name, product of Sumitomo Chemical Co., Ltd., Japan), etc. The preferable chelating resins to be used include, for example, Sumichelate (Sumitomo Chemical Co. Ltd., Japan), etc. The amount of resin to be added to the solution is in the range of about 1.2 to about 100 equivalents (exchange volume), preferably about 2 to about 50 equivalents per equivalent of the heavy metal ion. The treatment with the resin can be carried out at any temperature which is lower than a heat resisting temperature of the resin but at which no crystallization of DSTA occurs. It is preferably in the range of about 25° to about 60° C. The treatment completes within 1 minute to 4 hours irrespective of the treatment methods.

In the present invention oxalic acid can be used in place of the cation exchange resin or chelating resin in order to remove the heavy metal ion effectively. In this case oxalic acid is added to the solution of DSTA crude containing heavy metal ion and the mixture is refluxed with heating, followed by filtering off the resulting heavy metal oxalate. The amount of oxalic acid to be used is usually in the range of about 1.0 to about 20 moles, preferably about 1.2 to about 10 moles, per mole of the heavy metal ions contained in the DSTA crude. The refluxing is carried out preferably for 0.1 to 10 hours.

Then the DSTA crude dissolved in the solvent mixture is recrystallized by direct cooling or concentration and cooling to give highly purified DSTA. The DSTA concentration in the solvent at the time of recrystallization is preferably about 2 to about 70 wt. %, more preferably about 10 to about 50 wt. %.

The crystals thus precipitated are separated by filtration or centrifugation, washed with a small amount of cold solvent such as water, when required, and dried to obtain a highly purified DSTA.

The purified DSTA obtained in the present invention can be employed as starting materials for or modifiers of various resins such as polyimide, polyester, polyamideimide, polyesterimide or the like, as curing agents for epoxy resin or as starting materials for plasticizers, lubricating oils, medicines, agricultural chemicals, dyes, etc. For example, the polyimide resin prepared from diphenylsulfone-3,3',4,4'-tetracarboxylic acid as a starting monomeric compound is excellent in heat resistance, mechanical characteristics, electrical characteristics, etc. and has useful properties such as high solvent solubility, good processability, etc.

EXAMPLES

The invention will be described in greater detail with reference to the following examples, which in no way limit the invention. In examples purity or removal ratio of impurities in % shows the value as calculated from neutralization value.

REFERENCE EXAMPLE 1

In acetic acid were dissolved 274 g (1.0 mole) of 3,3',4,4'-tetramethyldiphenyl sulfone, 2.8 g (0.11 mole) of cobalt acetate and 44 g (0.45 mole) of ammonium bromide to obtain 2.7 liter of a solution. The solution was placed in an autoclave and heated at 140° C. The pressure in the autoclave was increased to 50 Kg/cm$^2$·G by injecting air. Oxidation reaction was conducted at the same temperature for 3 hours while air was injected continuously. The resulting reaction mixture was cooled and the precipitate was separated by filtration to obtain 366 g of crude of diphenylsulfone-3,3',4,4'-tetracarboxylic acid (hereinafter referred to as DSTA-1). The DSTA-1 crude thus obtained had a purity of 95.4%, and contained 16% of acetic acid and 5800 ppm of cobalt.

TheDSTA-1 crude (366 g) was dried to obtain 308 g of a crude of DSTA (hereinafter referred to as DSTA-2) which had a purity of 95.4%, and contained 0.7% of acetic acid and 5800 ppm of cobalt.

REFERENCE EXAMPLE 2

Crude diphenylsulfone-2,3,3',4'-tetracarboxylic acid (hereinafter referred to as DSTA-3) was obtained in the same manner as in Reference Example 1 except that 2,3,3',4'-tetramethyldiphenyl sulfone was used as a starting material. The DSTA-3 crude thus obtained had a purity of 94.8 % and contained 17% of acetic acid and 6200 ppm of cobalt.

EXAMPLE 1

The DSTA-2 crude (308 g) obtained in Reference Example 1 was dissolved in 1.5 liter of 7:3 volume ratio mixture of water and acetic acid at 100° C. The solution was cooled to room temperature (23° C.) for recrystallization. The precipitate was filtered off, washed with a small amount of cold water and dried to obtain 277 g of highly purified DSTA-2. The yield, removal ratio of impurities and cobalt content are shown in Table 1 below.

COMPARATIVE EXAMPLES 1 TO 5

The crude DSTA-2 (308 g) obtained in Reference Example 1 was dissolved in the predetermined amount of the solvent shown in Table 1 below at 100? C., and the solution was treated in the same manner as in Example 1 to obtain purified DSTA-2. The yield, removal ratio of impurities and cobalt content are shown in Table 1.

TABLE 1

| | Solvent | Amount (l) | Yield (%) | Removal ratio of impurities (%) | Cobalt content (ppm) |
|---|---|---|---|---|---|
| Ex. 1 | water-acetic acid mixture | 1.5 | 70 | 90.2 | 113 |
| Comp. Ex. 1 | water | 2.0 | 72 | 17.4 | 117 |
| Comp. Ex. 2 | glacial acetic acid | 3.0 | 63 | 69.1 | 536 |
| Comp. Ex. 3 | dioxane | 1.5 | 57 | 46.4 | 2100 |
| Comp. Ex. 4 | water-dioxane mixture (7:3 in volume) | 1.5 | 49 | 47.1 | 188 |
| Comp. Ex. 5 | water-methanol mixture (8:2 in volume) | 1.0 | 52 | 37.0 | 124 |

EXAMPLE 2

The DSTA-I crude (366 g) obtained in Reference Example 1 was dissolved in 1.5 liter of 7:3 volume ratio mixture of water and acetic acid at 100? C. The solution was cooled to room temperature (23° C.) for recrystallization. The precipitate thus obtained was filtered off, washed with a small amount of cold water and dried to obtain 283 g of highly purified DSTA-1 (yield 72%, purity 99.0%, cobalt content 121 ppm).

EXAMPLE 3

The DSTA-1 crude (366 g) obtained in Reference Example 1 was dissolved in 3.0 liter of 9:1 volume ratio mixture of water and acetic acid at 100° C. To the solution was added 350 ml of "DIAION PK-216" (trade name, cation exchange resin, product of Mitsubishi Kasei Corporation, Japan). The mixture was stirred at 60° C. for 1 hour. The resin was filtered off and the filtrate, after concentrated to about ½ volume, was cooled to room temperature (23° C.) for recrystallization. The precipitate was filtered off, washed with a small amount of cold water and dried to obtain 279 g of highly purified DSTA-1 (yield 71%, purity 99.4%, cobalt content 16 ppm).

EXAMPLE 4

The DSTA-1 crude (366 g) obtained in Reference Example 1 was dissolved in 2.5 liter of 4:6 volume ratio mixture of water and acetic acid at 100° C. To the solution was added 20 g (0.22 mole) of oxalic acid. The mixture was refluxed at 102° C. for 1 hour and the resulting insoluble (oxalate) was filtered off at about 80° C. The filtrate was cooled to room temperature (23° C.) for recrystallization. The precipitate was filtered off, washed with a small amount of cold water and dried to obtain 264 g of highly purified DSTA-1 (yield 67%, purity 99.0%, cobalt content 14 ppm).

EXAMPLE 5

The DSTA-3 crude obtained in Reference Example 2 was dissolved in 1.5 liter of 7:3 volume ratio mixture of water and acetic acid at 100° C. The solution was cooled to room temperature (23° C.) for recrystallization. The precipitate thus obtained was filtered off, washed with a small amount of cold water and dried to obtain 271 g of highly purified DSTA-2 (yield 69%, purity 99.1%, cobalt content 108 ppm).

I claim:

1. A method for purifying a diphenylsulfone tetracarboxylic acid produced by oxidizing the corresponding tetraalkyldiphenylsulfone in the presence of a cobalt-containing catalyst and containing cobalt ion as an impurity, which comprises dissolving the said diphenylsulfone tetracarboxylic acid in a solvent mixture of water and acetic acid, recrystallizing the diphenylsulfone tetracarboxylic acid from the solvent mixture and separating purified diphenylsulfone tetracarboxylic acid from the solvent mixture.

2. A method according to claim 1, wherein the solvent mixture has an acetic acid concentration of 2 to 90 vol. %.

3. The method according to claim 2, wherein the concentration of the acetic acid is 10 to 70 vol.

4. A method according to claim 1, wherein the solution of the diphenylsulfone tetracarboxylic acid in the solvent mixture of water and acetic acid is treated with a cation exchange resin prior to recrystallizing the diphenylsulfone tetracarboxylic acid from the solvent mixture.

5. A method according to claim 1, wherein the solution of the diphenylsulfine tetracarboxylic acid in the solvent mixture of water and acetic acid is treated with a chelating resin prior to recrystallizing the diphenylsulfone tetracarboxylic acid from the solvent mixture.

6. A method according to claim 1, wherein the solution of the diphenylsulfone tetracarboxylic acid in the solvent mixture of water and acetic acid is treated with oxalic acid to remove the cobalt ion in the form of cobalt oxalate prior to recrystallizing the diphenylsulfone tetracarboxylic acid from the solvent mixture.

7. The method according to claim 1, wherein the diphenylsulfone tetracarboxylic acid has the following formula:

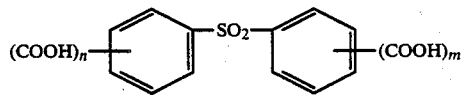

wherein m and n are each an integer of 0 to 4, and the sum of m and n is 4.

8. The method according to claim 7, wherein m is 2 and n is 2.

9. The method according to claim 7, wherein the diphenylsulfone tetracarboxylic acid is diphenylsulfone-3,3′4,4′-tetracarboxylic acid or diphenylsulfone-2,3,3′,4′-tetracarboxylic acid.

* * * * *